US010072961B2

(12) United States Patent
Griessbaum et al.

(10) Patent No.: US 10,072,961 B2
(45) Date of Patent: Sep. 11, 2018

(54) LEVEL MEASURING INSTRUMENT FOR DETERMINING MOISTURE CONTENT

(71) Applicant: VEGA Grieshaber KG, Wolfach (DE)

(72) Inventors: Karl Griessbaum, Muhlenbach (DE); Josef Fehrenbach, Haslach (DE); Roland Welle, Hausach (DE)

(73) Assignee: VEGA GRIESHABER KG, Wolfach (DE)

( * ) Notice: Subject to any disclaimer, the term of this patent is extended or adjusted under 35 U.S.C. 154(b) by 32 days.

(21) Appl. No.: 14/787,936

(22) PCT Filed: Jun. 3, 2014

(86) PCT No.: PCT/EP2014/061431
§ 371 (c)(1),
(2) Date: Oct. 29, 2015

(87) PCT Pub. No.: WO2014/198582
PCT Pub. Date: Dec. 18, 2014

(65) Prior Publication Data
US 2016/0138956 A1 May 19, 2016

(30) Foreign Application Priority Data
Jun. 11, 2013 (DE) .................... 20 2013 102 514 U

(51) Int. Cl.
G01F 23/284 (2006.01)
G01N 22/04 (2006.01)
G01F 23/24 (2006.01)
G01F 23/00 (2006.01)

(52) U.S. Cl.
CPC ........ *G01F 23/284* (2013.01); *G01F 23/0076* (2013.01); *G01F 23/246* (2013.01); *G01F 23/2845* (2013.01); *G01N 22/04* (2013.01)

(58) Field of Classification Search
CPC .. G01F 23/284; G01F 23/0076; G01F 23/246; G01F 23/2845; G01N 22/04
USPC ........................................... 73/292
See application file for complete search history.

(56) References Cited

U.S. PATENT DOCUMENTS 2,704,891 A * 3/1955 Ferrier ................ G01F 23/0023
137/404
3,813,927 A * 6/1974 Furgason ............... G01N 25/56
73/73
4,991,915 A 2/1991 Thompson et al.
(Continued)

FOREIGN PATENT DOCUMENTS

DE 296 17 488 6/1997
EP 1 308 725 5/2003
(Continued)

Primary Examiner — Son Le
Assistant Examiner — Marrit Eyassu
(74) Attorney, Agent, or Firm — Fay Kaplun & Marcin, LLP

(57) ABSTRACT

Described is a method and system for a level measurement. An echo curve is analyzed, and both the level and the moisture content of the stored material is determined therefrom. The level measuring instrument works in such an energy-saving manner that it is sufficient to supply the instrument with power using a 4 . . . 20 mA two-wire conductor loop that is also used to transmit at least some of the measured values.

21 Claims, 4 Drawing Sheets

(56) References Cited

U.S. PATENT DOCUMENTS

Figure 4:
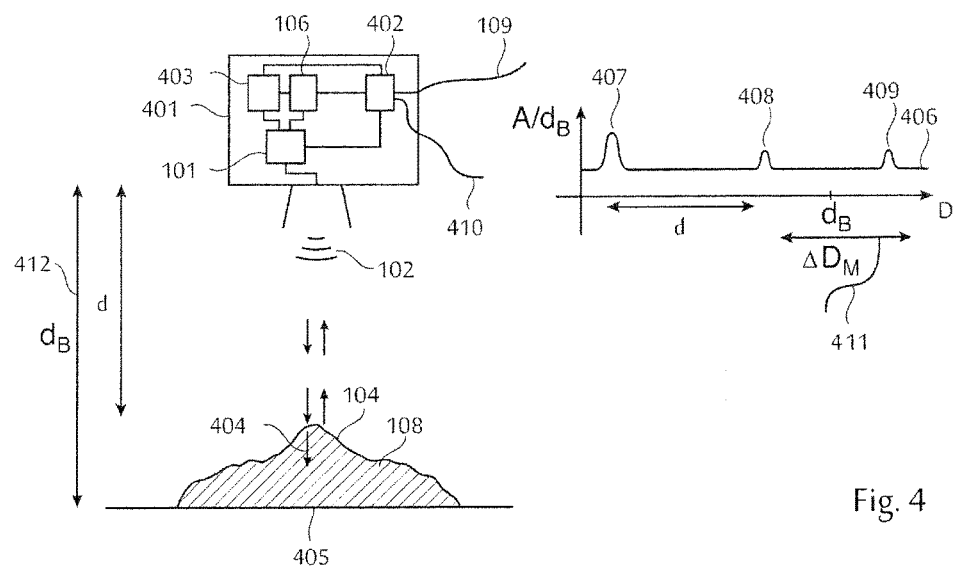

| | | | | |
|---|---|---|---|---|
| 5,767,685 A | * | 6/1998 | Walker | G01N 22/04 324/632 |
| 6,257,049 B1 | * | 7/2001 | Greybush | G01N 22/04 324/640 |
| 6,539,794 B1 | * | 4/2003 | Otto | G01F 23/284 340/621 |
| 7,525,476 B1 | | 4/2009 | Delin et al. | |
| 9,068,876 B2 | | 6/2015 | Griessbaum et al. | |
| 2003/0035462 A1 | * | 2/2003 | Savoie | G01F 23/246 374/141 |
| 2003/0191588 A1 | * | 10/2003 | Kohler | G01N 22/04 702/50 |
| 2004/0031335 A1 | * | 2/2004 | Fromme | G01B 11/24 73/865 |
| 2005/0253595 A1 | * | 11/2005 | France | G01N 22/04 324/639 |
| 2006/0028213 A1 | * | 2/2006 | Typpo | D21G 9/0027 324/640 |
| 2007/0018657 A1 | * | 1/2007 | Nagata | G01N 22/04 324/636 |
| 2011/0093212 A1 | * | 4/2011 | Herrmann | G01N 22/04 702/23 |
| 2011/0094299 A1 | | 4/2011 | Muller et al. | |
| 2012/0174665 A1 | * | 7/2012 | Wimberger | G01D 21/02 73/295 |
| 2012/0234074 A1 | * | 9/2012 | Hagen | G01F 1/32 73/1.73 |
| 2013/0118252 A1 | * | 5/2013 | Hartmann | G01F 23/2962 73/290 V |
| 2014/0298903 A1 | * | 10/2014 | Goto | G01F 23/22 73/292 |
| 2015/0000396 A1 | * | 1/2015 | Maguin | F01N 3/2066 73/290 V |

FOREIGN PATENT DOCUMENTS

| | | | | |
|---|---|---|---|---|
| EP | 1308725 A1 | * | 5/2003 | B28C 7/024 |
| EP | 1 321 565 | | 6/2003 | |
| EP | 1321565 A1 | * | 6/2003 | D06F 58/28 |
| EP | 2 527 802 | | 11/2012 | |
| WO | WO 90/07110 | | 6/1990 | |
| WO | 2003/016835 | | 2/2003 | |
| WO | 2003/001160 | | 1/2009 | |

\* cited by examiner

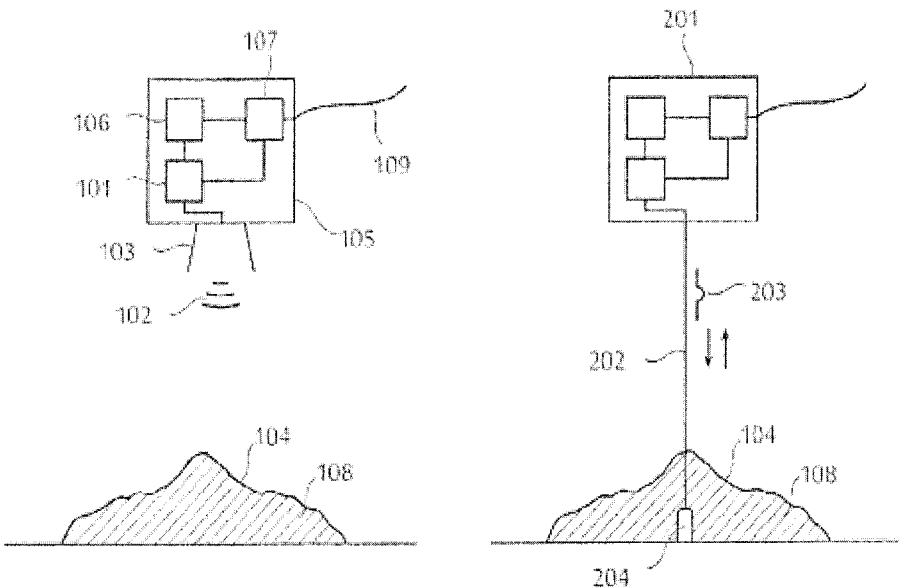
Fig. 1
PRIOR ART
Fig. 2
PRIOR ART
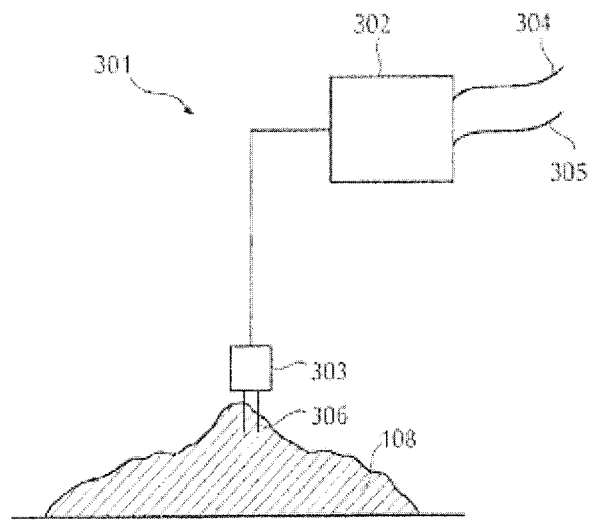
Fig. 3
PRIOR ART

LEVEL MEASURING INSTRUMENT FOR DETERMINING MOISTURE CONTENT

FIELD OF THE INVENTION

The invention relates to level measurement. In particular, the invention relates to a level measuring instrument for determining a level of a stored material, to a program element and to a machine-readable medium.

TECHNICAL BACKGROUND

There are currently numerous sensors on the market for detecting the level in a container or on a stockpile. Sensors that detect the level using guided radar waves or radar waves that radiate into free space are particularly important.

These level measuring instruments can work on the principle of the pulse transit-time technique. In this case, electromagnetic pulses are transmitted towards the stored-material surface. The level measuring instrument then receives the signal components of this measurement signal that are reflected at the stored-material surface and at other reflectors if applicable, and generates therefrom an echo curve, which can be analysed to determine the level.

Level measuring instruments that work on the FMCW principle (FMCW: Frequency Modulated Continuous Wave) are also known. Again these can use guided signals or signals radiated into free space.

Particularly for users from the grain processing sector, but also for users from the gravel/concrete industry, there is an additional need for measuring instruments for continuous detection of the moisture (moisture content) of the material stored in the container or on the stockpile.

If the moisture content of the material stored in a container or on a stockpile (stored material) is intended to be measured, then a moisture meter is used for this purpose, as shown in FIG. 3 for example.

The moisture meter uses a direct time-measurement technique to determine the transit time of a measurement signal along a measuring probe located in the stored material. The relatively short time periods for which the measurement signal travels along the measuring probe through the stored material can result in inaccurate measurements. The measurement accuracy can be improved by averaging a plurality of measurements, although this greatly increases the power consumption of the moisture meter. This power consumption is then too high for a two-wire device.

SUMMARY OF THE INVENTION

The present invention relates to a measuring instrument for determining the moisture content of a material, which instrument has a low power consumption. In addition, the present invention relates to a measuring instrument for determining the moisture content of a material, which instrument more accurately provides the measured value for the moisture content of the stored material.

According to a first aspect of the invention, a level measuring instrument for determining a level of a stored material is defined that comprises a radio frequency unit and a signal processing unit. The radio frequency unit is used to generate a measurement signal, which is subsequently emitted towards the stored-material surface either by radiating into free space or by guided means.

This measurement signal is then reflected entirely or in part at the stored-material surface and at one or more additional reflectors, such as the container base, a probe end or other discontinuities. The reflected measurement signal is than fed to the signal processing unit of the level measuring instrument, which unit derives an echo curve from said signal and then determines the level from this echo curve.

In addition, the level measuring instrument is able to determine in addition from this echo curve the moisture content or at least a characteristic value for the moisture content (i.e. a value associated with the moisture content) of the stored material.

This can save power compared with known methods and devices because both the level and the moisture content can be determined from a single measurement.

There is no direct transit-time measurement using an additional probe but instead an analysis is performed on a measurement already carried out in the process of determining the level.

According to one embodiment of the invention, a level measuring instrument for determining a level of a stored material is defined that determines a measured value for the current level and also a measured value for the moisture content of the stored material from two amplitude values of two echoes in an echo curve and from a separation of two echoes in the same echo curve. The moisture content of the medium can be more accurately provided by using information on amplitude and separation. It can be particularly advantageous to process the information in such a way that both the measured value for the level and the measured value for the moisture content can be determined and provided in a very accurate manner which incurring low circuitry costs and/or power costs.

According to one embodiment of the invention, the level measuring instrument is designed for connection to a two-wire conductor loop, for example a 4 . . . 20 mA two-wire conductor loop. It comprises a two-wire interface, for instance a 4 . . . 20 mA two-wire interface, for this purpose. The electrical power required for operating the instrument can be supplied via this two-wire conductor loop. The two-wire conductor loop can also be used to transmit to an external location all or a subset of the measured values associated with the level and/or the moisture content.

Alternatively or additionally it can be provided that some of the measured values (for example the moisture content measured values or the level measured values) are transmitted via a second data interface, which may be in the form of a second two-wire interface or as a data bus interface for example.

According to another embodiment of the invention, the measurement signal is an FMCW signal. In other words, the level measuring instrument is a measuring instrument that works on the FMCW principle and emits frequency modulated continuous waves as the measurement signal.

According to another embodiment of the invention, the measurement signal is an electromagnetic pulse. In this case, the level measuring instrument is a radar level indicator operating on the principle of the pulse transit-time technique.

According to another embodiment of the invention, the level measuring instrument comprises a two-wire interface, wherein the level measuring instrument is designed to be supplied with power and to output all the measured values from the level measuring instrument via the two-wire interface.

According to another embodiment of the invention, the level measuring instrument comprises, in addition to the two-wire interface, an additional data interface, wherein the level measuring instrument is designed to be supplied with power and to output a first measured value, selected from the group of the measured level and moisture-content values, via the two-wire interface, and wherein the level measuring instrument is designed to output a second measured value, selected from the group of measured level and moisture-content values, via the data interface.

The data interface may be a second two-wire interface or, for example, a data bus interface.

According to another embodiment of the invention, the measuring instrument is designed to use electromagnetic waves radiating into free space as the measurement signal.

According to another embodiment of the invention, the level measuring instrument is designed as a measuring instrument for using guided electromagnetic waves as the measurement signal. In this case it has a measuring probe (waveguide apparatus) which extends at least in part into the stored material (at least if the level is suitably high).

According to another embodiment of the invention, the level measuring instrument has a waveguide apparatus which comprises a plurality of reflectors spaced apart from one another along a longitudinal extension direction of the waveguide apparatus. In this case, the level measuring instrument is designed to determine a moisture profile from the echo curve, which profile extends along the longitudinal extension of the waveguide apparatus. In order to create the moisture profile, the various reflectors arranged along the waveguide apparatus are needed because each reflector reflects some of the measurement signal, and these reflections can then be detected in the recorded echo curve.

One aspect of the invention thus relates to a field device for the combined measurement of level and moisture content of a material in a container or on a stockpile, the supply and measured-value output being provided via only one conductor pair.

In particular, both characteristic values (level and moisture content) can be measured from the reflection of a pulsed electromagnetic wave and from determining the amplitude and time of the reflected wave components using the technique of sequential sampling.

It can also be provided for the supply and measured-value output to occur via precisely two conductor pairs, one conductor pair being a 4 . . . 20 mA conductor loop for supplying the field device and outputting one measured value, and the other conductor pair being a 4 . . . 20 mA conductor loop (passive) for outputting the other measured value.

By using the same measurement signals for both measurements (level and moisture content), the power consumption increases only negligibly compared with known sensors that are intended solely for one of the two measurements. This means that a two-wire device is suitable for the combined sensor.

Measuring both characteristic values from the reflection of a pulsed electromagnetic wave and from determining the amplitude and time of the reflected wave components using the technique of sequential sampling is advantageous in that the same measurement signals to be used.

In addition, a method is defined for determining a level of a stored material, in which a measurement signal is generated, the level is determined from an echo curve of the measurement signal, and a moisture content of the stored material is determined from this same echo curve.

According to another embodiment of the invention, electrical power is supplied via a two-wire conductor loop, for example a 4 . . . 20 mA current loop, to an instrument performing the method.

The measured values can also be output via this two-wire conductor loop. As already described above, it can also be provided that some of the measured values are output via another interface.

A two-wire conductor loop may specify an installation arrangement of a field device (for example of a level measuring instrument, moisture meter, etc.) in which the device is supplied with the required power solely via a single conductor pair and at least one measured value is output simultaneously via this conductor pair.

A two-wire interface may be an interface of a field device (for example of a level measuring instrument, moisture meter, etc.) via which the device can be operated within a two-wire conductor loop. A two-wire interface may be selected from the group of standard interfaces: 4 . . . 20 mA current loop, 4 . . . 20 mA current loop with HART, Profibus, PA, Foundation Fieldbus.

A two-wire device may be a field device (for example a level measuring instrument, moisture meter, etc.) that has at least one two-wire interface.

According to another aspect of the invention, a program element is defined that, when executed on a processor, instructs the processor to perform the steps described above and below.

According to another aspect of the invention, a machine-readable medium is defined on which a program element is stored which, when executed on a processor, instructs the processor to perform the method steps described above and below.

It should be pointed out that the level measuring instruments described above and below can be designed to perform all the method steps described here and below.

The program element can be part of a piece of software that is stored on a processor of a measuring instrument. In this case, the processor is also the subject matter of the invention. The invention also relates to a program element that, by means of an update, causes an existing program to use the invention.

Embodiments of the invention are described below with reference to the figures.

SHORT DESCRIPTION OF THE FIGURES

Figure 5:
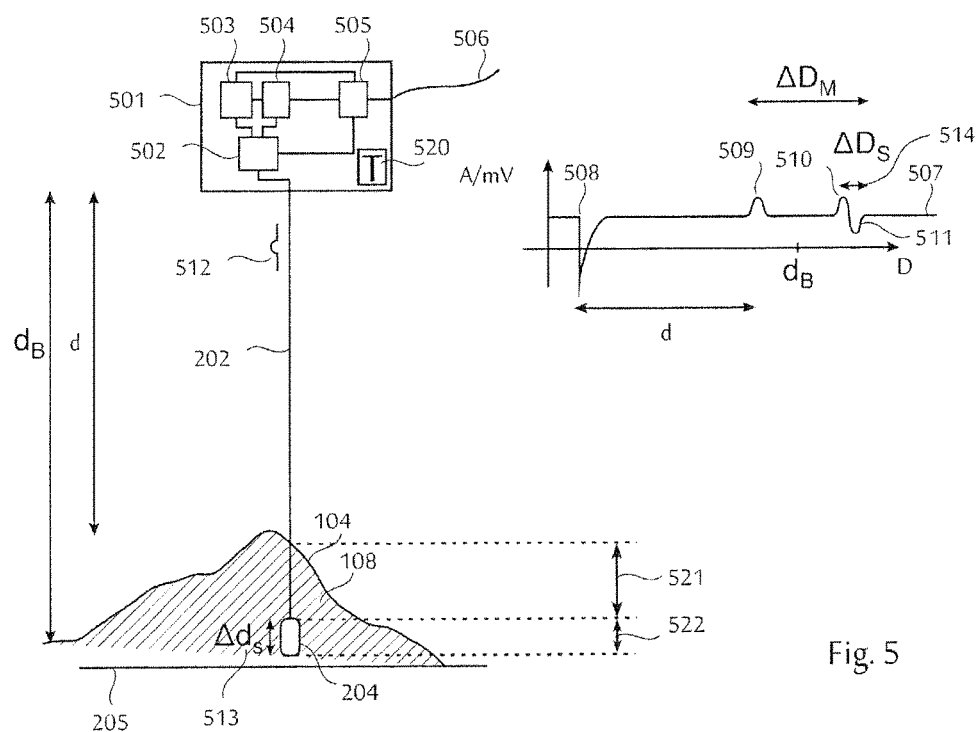
Figure 6:
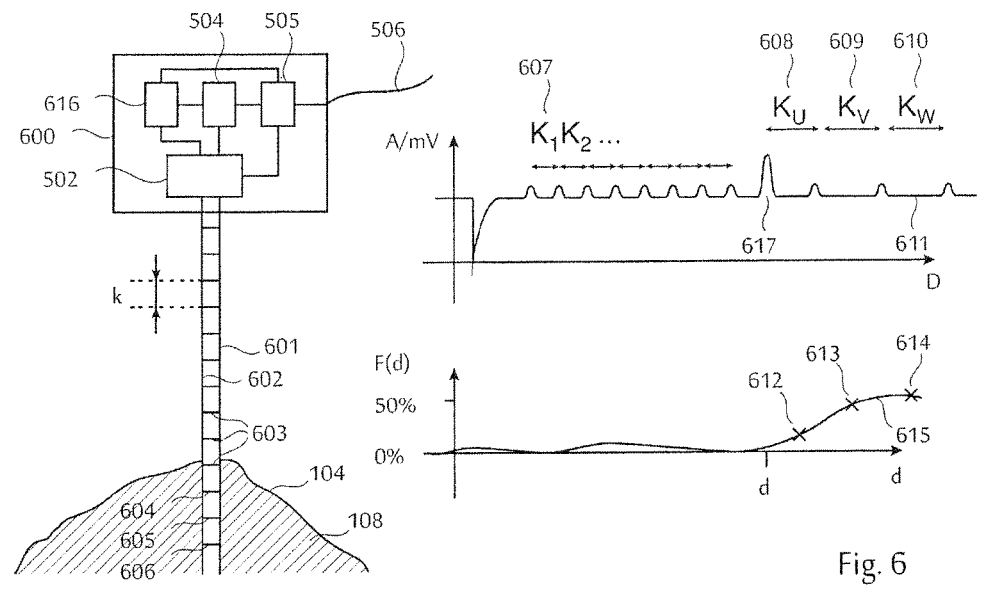
Figure 7:
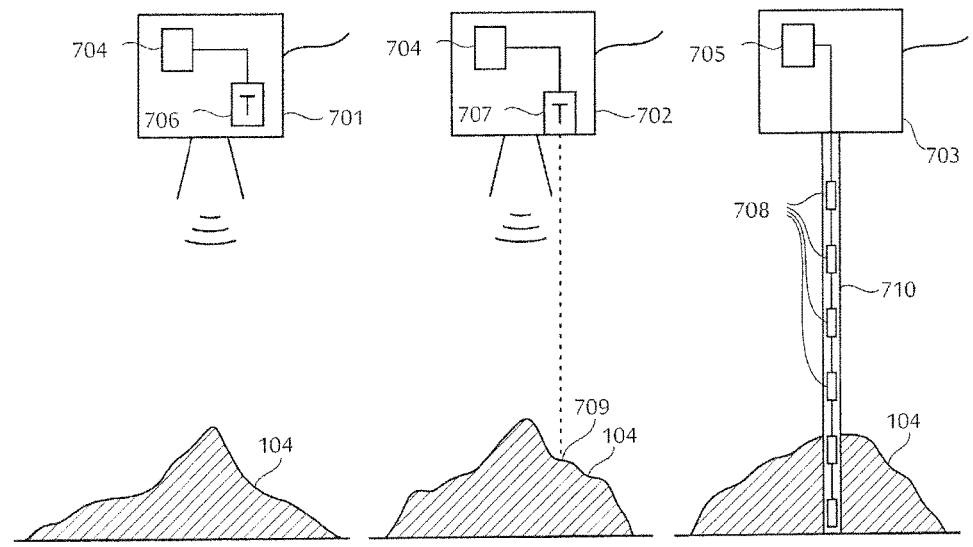
Figure 8:
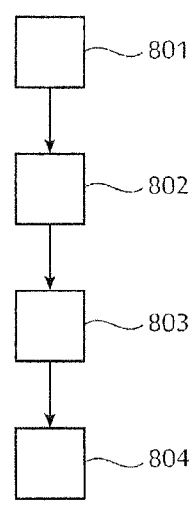

FIG. 1 shows a radar level indicator.
FIG. 2 shows a level measuring instrument that operates on the principle of guided microwaves.
FIG. 3 shows a moisture meter.
FIG. 4 shows a level measuring instrument according to one embodiment of the invention.
FIG. 5 shows a level measuring instrument according to another embodiment of the invention.
FIG. 6 shows a level measuring instrument according to another embodiment of the invention.
FIG. 7 shows three level measuring instruments according to other embodiments of the invention.
FIG. 8 shows a flow diagram of a method.

DETAILED DESCRIPTION OF EMBODIMENTS

The depictions in the figures are schematic and not to scale.

Where the same reference signs are used in different figures in the following description of the figures, they denote the same or similar elements. The same or similar elements may also be denoted by different reference signs, however.

FIG. 1 shows a radar level measuring instrument 105 according to the prior art. The radar instrument uses a radio frequency unit 101 to generate a radio frequency measurement signal 102, and emits this signal via a suitable antenna 103 towards a stored-material surface 104. The signal 102 is reflected at this surface and after a relevant transit time arrives back at the level measuring instrument 105, where it is processed in a known manner by the radio frequency unit 101 and transferred to an analysis unit 106. This unit calculates the distance to the stored material 104 on the basis of the transit time.

Level measuring instruments 105 that are supplied with power via a 4 . . . 20 mA current loop 109 in particular are commercially important. In this case, the level measuring instrument 105 comprises a suitable power supply 107, which in particular contains an energy storage unit and an energy control unit, and which controls the other components in the sensor in a suitable manner to ensure a stable measurement operation. The level value measured by the sensor can be provided externally in analogue form via the 4 . . . 20 mA interface 106.

It is also possible to provide the measured value in digital form, for example using HART, Profibus, FF or Modbus.

In addition, it is possible to measure the level using guided microwaves. FIG. 2 shows a corresponding instrument. Unlike a radar instrument 105 that radiates into free space, the instrument based on the principle of guided microwaves comprises a suitable waveguide 202, which guides a measurement signal 203 to the stored-material surface 104 and back again to the measuring instrument 201. The measured value is measured in a similar manner to that in the radar instrument 105. The instrument can likewise provide the determined measured value externally via a 4 . . . 20 mA interface or digital fieldbuses.

On the other hand, dedicated moisture meters can be used to determine the moisture content of the medium 108 to be measured. FIG. 3 shows such a measuring instrument. The measuring instrument 301 can consist of a probe unit 303 comprising one or more individual probes 306. Guided microwaves are used to measure the transit time of the signal along the probe, which is located entirely in the medium, and this transit time is passed to a measurement converter unit 302, which provides the control and power supply for the probe unit 303.

The measurement converter unit 302 calculates a relative permittivity $\varepsilon'_R$ from the transit times of the signal along the probe 306, which permittivity can be converted into a moisture value F by taking into account media properties, which must be set in advance. To a good approximation, a proportional characteristic can be assumed here:

$$F = c \cdot \varepsilon'_R$$

where c is a constant that depends on the medium (and possibly the temperature) and is known in advance for the stored medium.

The calculated moisture value can be provided externally at a suitable digital interface 304, for instance RS-232.

In addition, the moister meter 302 usually comprises a further interface 305, which supplies the sensor unit 301 with power.

These sensors are not intended to be used to measure level and moisture content simultaneously. Furthermore, moisture meters measure the transit time along the measuring probes 306 by means of direct time-measurement techniques, which can result in large measurement errors owing to the extremely short time periods. The accuracy can be improved by averaging a plurality of measurements, which in turn greatly increases the power consumption of the moisture meter 301 and consequently prevents implementation as a 4 . . . 20 mA two-wire device.

FIG. 4 shows a first embodiment of a level measuring instrument, which combines the measurement of level and moisture content in a two-wire measuring instrument for connecting to a 4 . . . 20 mA two-wire conductor loop.

The measuring instrument 401 has a radio frequency unit 101, a signal processing unit 106 and a modified power supply unit 402. In addition, the measuring instrument 401 has a moisture calculation unit 403.

The measuring instrument 401 transmits a radio frequency signal 102 towards the medium 108 to be measured. Part of the microwave energy is reflected at the surface 104 of the medium 108 and arrives back at the measuring instrument 401 after an appropriate transit time.

Another part of the microwave energy 404 penetrates the medium 108 and is not reflected until the lower limit 405 of the medium. The lower limit is often provided by the container base. The radio frequency unit 101 processes the received signals and can use known techniques to provide an echo curve 406 in digital or analogue form. In addition to the antenna echo 407 resulting from immediate reflections inside the antenna, the echo curve contains the level echo 408 originating from the reflection at the surface 104 and additionally the base echo 409 resulting from the reflection at the container base 405.

The signal processing unit 106 can use known methods for calculating the distance d to the stored-material surface, on the basis of the echo curve 406. The calculated distance can be provided in analogue form at a 4 . . . 20 mA interface 109. Alternatively or additionally, the value can be provided via a digital interface.

After calculating the distance d to the stored-material surface, the moisture calculation unit 403 uses the echo curve 406 and the distance d to the stored-material surface to calculate the moisture content of the medium 108. For this purpose, the material characteristic values can be preset as parameters in the moisture calculation unit 403. It should be mentioned here that the moisture calculation unit 403 may be provided as part of the signal processing unit or as a separate component.

Various methods can be used to calculate the material moisture content F itself. One option is to analyse the amplitude $A_L$ of the stored-material echo 408, from which the moisture content can be deduced when material characteristic values are known. To a good approximation, the following holds:

$$F = c \cdot \left( \frac{A_E - A_L}{A_E + A_L} \right)^2$$

where c is a constant that depends on the medium (and possibly the temperature) and is known in advance, $A_E$ is the maximum amplitude of the signal emitted by the level measuring instrument, and $A_L$ is the amplitude of the stored-material echo.

Another option is to analyse the attenuation of the microwave signals 102 in the material 108, which can be calculated from the amplitude of the stored-material echo 408 and from the amplitude of the base echo 409. The moisture content of the medium can be deduced from the attenuation in a known manner using specific material characteristic values.

The attenuation coefficient α is defined by:

$$\alpha = \frac{2\pi}{\lambda_0} \cdot \sqrt{\frac{\varepsilon'_R}{2}} \cdot \sqrt{\sqrt{1+\left(\frac{\varepsilon''_R}{\varepsilon'_R}\right)^2} - 1}$$

where
$\lambda_0$ is the wavelength of the signal used for the measurement
$\varepsilon'_R$ is the real part of the complex relative permittivity
$\varepsilon''_R$ is the imaginary part of the complex relative permittivity The attenuation $D_M$ in the medium can be calculated from measurements using the following equation:

$$D_M = \frac{A_B}{\left(\sqrt{A_H} - \sqrt{\frac{A_L^2}{A_H}}\right)^2}$$

where
$A_B$ is the amplitude of the base echo
$A_H$ is the maximum amplitude of the signal emitted by the level measuring instrument
$A_L$ is the amplitude of the stored-material echo The distance $d_B$ to the container base, which is already known, and the current distance d to the stored material, can be used to calculate the attenuation coefficient α using:

$$\alpha = \frac{D_M}{d_B - d}$$

Taking into account already known material-specific or negligibly small characteristic values for the imaginary part of the relative permittivity, the real part of the relative permittivity can be determined by transformation and can be used to directly deduce the moisture content of the medium. These non-linear relationships can be converted and solved in the instrument in particular using numerical approximation techniques.

In a third variant, the moisture may also be calculated from the separation $\Delta D_M$ 411 of the stored-material echo 408 from the base echo 409 using the container height $d_S$ 412 and material-dependent characteristic values.

The phase coefficient β is defined by:

$$\beta = \frac{2\pi}{\lambda_0} \cdot \sqrt{\frac{\varepsilon'_R}{2}} \cdot \sqrt{\sqrt{1+\left(\frac{\varepsilon''_R}{\varepsilon'_R}\right)^2} + 1}$$

where
$\lambda_0$ is the wavelength of the signal used for the measurement
$\varepsilon'_R$ is the real part of the complex relative permittivity
$\varepsilon''_R$ is the imaginary part of the complex relative permittivity The phase rotation in the medium can be evaluated from measurements on the basis of the increase in the separation $\Delta D_M$ (411) between the stored-material echo and the base echo. The following holds:

$$\frac{\Delta D_M}{d_B - d} = \sqrt{\frac{\varepsilon'_R}{2}} \cdot \sqrt{\sqrt{1+\left(\frac{\varepsilon''_R}{\varepsilon'_R}\right)^2} + 1}$$

where
$d_B$ is the physical distance from the measuring instrument to the container base
d is the physical distance from the measuring instrument to the stored-material surface Taking into account already known material-specific or negligibly small characteristic values for the imaginary part of the relative permittivity, the real part of the relative permittivity can be determined by transformation and can be used to directly deduce the moisture content of the medium. These non-linear relationships can be converted and solved in the instrument, in particular using numerical approximation techniques.

It may also be possible to combine at least two of the methods mentioned above. For instance it may be advantageous particularly to evaluate within a single measurement both the attenuation of the signal within the medium and the phase rotation represented in the increase in the separation $\Delta D_M$, and then to calculate from the above equations, using numerical techniques, the exact values for the real and imaginary parts of the relative permittivity. It may thereby be possible to measure the moisture in the material even more accurately.

The calculated moisture value can be passed to the communications unit 402, which provides said value externally. For this purpose, the sensor may have a second analogue 4 . . . 20 mA interface 410. It may also be possible, however, to provide the characteristic value in analogue and/or digital form at the existing interface 109.

It should be mentioned at this point that, in the context of the present invention, a moisture content or a moisture value or a moisture level may be at least one value selected from the group of measurable values comprising gravimetric moisture content, percentage of moisture by mass, percentage of dry matter by mass, volumetric moisture content and percentage of moisture by volume.

The modified power supply unit 402 ensures that the actual measurement-data acquisition procedure is stable. Only a minimum amount of extra power needs to be supplied compared with existing instruments purely for level measurement, because the actual energy-intensive process of echo-curve acquisition in the radio frequency unit 101 must only be performed once per measurement cycle, as in a conventional level measuring instrument. Calculating the moisture characteristic values in the unit 403 may be implemented in combination with the signal processing 106 in the form of software algorithms in a processor that already exists anyway, and requires only a minimum of extra power.

It may also be a special feature of the measuring instrument that the echo curve can be acquired in the radio frequency unit 101 in a particularly energy-saving manner by means of a sequential sampling technique. This results in a significant power saving compared with direct time-measurement techniques such as those that can be used in pure moisture meters, allowing the combined sensor to be designed as a two-wire measuring instrument. Further advantages of the sequential sampling technique also include an increased dynamic response, which also allows detection of very small echoes, and a higher measurement rate.

FIG. 5 shows another embodiment of a measuring apparatus. The measuring instrument 501 works on the principle of guided microwaves and transmits radio frequency measurement signals along a waveguide apparatus 202 towards the medium 108 to be measured. The waveguide apparatus may be implemented in an electrically insulated or non-insulated form by a cable, a rod, a coaxial conductor or by arrangements of a plurality of rods or cables. It may also be possible to fix the waveguide apparatus by tensioning weights 204 along the path to be measured in the case of the design using cables. In addition, there may also be anchorage (not shown) to the container base 205.

The measuring instrument 501 can consist of the radio frequency unit 502 also present in other level measuring instruments, the signal processing unit 504 and the interface to a higher-level controller 506, which is typically implemented as a 4 . . . 20 mA interface. Furthermore, the measuring instrument 501 has a moisture calculation unit 503 and a power-supply and communications unit 505.

A temperature measuring device 520 can also be provided. The temperature measuring device 520, also referred to below as a temperature sensor, can be located, for example, in or on the tensioning weight 204. Alternatively or additionally to this, a temperature measuring device 706, 707 can be arranged inside the measuring instrument 501, as shown in FIG. 7.

The temperature measured inside the sensor can be converted into an estimate of the temperature of the medium 108 using factory-measured characteristic values and taking into account the length L of the probe 202, which length may be factory-specified for example. The temperature measurement can be located particularly advantageously immediately beside the outlet point of the probe 202 in the measuring instrument 501. This structural design allows the thermal conductivity of the metal probe 202 to be used to indirectly measure the temperature of the medium 108. A constant heat flow is established inside the probe 202 over the measurement cycle concerned. The temperature of the medium can be directly deduced from the distance of the medium from the measuring instrument (equals the current level value) and the thermal conductivity of the metal in conjunction with the measured temperature change at the outlet of the probe.

Further improvements are obtained when the cooling effect of the connection of the probe 202 to the sensor 501 is taken into account. If this connection is considered as a cooling body, then its cooling capacity can be ascertained in advance at the factory. Any effected changes in the heat dissipated by the cooling body can be taken into account in the calculation if the prevailing ambient temperature is measured by means of a second temperature sensor (not shown here) on the outer wall 501 of the sensor. Measuring the temperature difference that actually exists on the resultant cooling body allows calculation of the heat flow, from which the temperature of the medium can be directly deduced, again taking into account the thermal conductivity (Fourier's law).

The temperature measuring device measures a temperature value, which can be used to improve the accuracy with which the moisture content is determined.

The measured temperature values can significantly improve the determination of the moisture value on the basis of the echo curve acquired by the level measuring instrument.

A rule for correcting the moisture content of the stored product as a function of the temperature can be hardcoded into the level measuring instrument for instance when the instrument is being manufactured, so that the relevant temperature compensation curves can be directly accessed during operation of the measuring instrument.

Alternatively or additionally, an interface for an external temperature sensor, for example a PT 100, can be provided on the measuring instrument or on the tensioning weight.

The temperature sensor can be designed to transmit to the electronics 502-505 of the measuring instrument the acquired data via a data-transmission and power-supply line assembly arranged in the waveguide 202, which is in the form of a cable for example.

It can be provided that the measuring instrument determines the moisture content in two or more regions of the measuring probe that include tensioning weights 202, 204 by analysing different segments of the echo curve. A moisture curve in the form of a two-level or multi-level step function can be determined in this manner.

For example, the region of the echo curve attributable to the region 521 of the measuring probe located in the stored material can be used as the first moisture measurement region. The region of the echo curve attributable to the length 522 of the tensioning weight 204 or of another reference body can be used as the second moisture measurement region.

The moisture curve can be determined in a similar way also for level measuring instruments that perform non-contact measurements. The holes in a standpipe or reference measurement point(s) made in the container can be used as reflectors that can be identified in the echo curve.

The measuring instrument 501 first detects an echo curve 507, which reproduces the reflection conditions along the waveguide 202. The echo curve 507 initially contains the echo 508 from the junction with the waveguide 202 and also the stored-material echo 509 generated by the stored-material surface 104. In the present example, the waveguide apparatus 202 has a tensioning weight 204, which is depicted by two echoes 510, 511 in the echo curve, the first echo identifying the start of the tensioning weight and the second echo identifying the end of the tensioning weight.

A measurement cycle in the measuring instrument 501 may proceed in the same way as in the radar instrument 401 described above. The same techniques and approaches may also be used to actually determine the material moisture content.

Furthermore, there are additional options for determining the moisture content of the material 108.

In theory, the propagation speed of a microwave signal 512, 102 in a medium 108 is reduced according to the material properties (relative permittivity, granularity, compaction) and according to the moisture content of the material. In terms of measurements, this can be identified in the echo curve by the separation between two reflection points within the medium appearing larger in the echo curve. In the example shown in FIG. 5, the physical distance $\Delta d_S$ 513 between the upper end and lower end of the tensioning weight 204 appears significantly larger in the echo curve 507 ($\Delta D_S$, 514).

From the measured increase in the separation of these two echoes, it is possible to use the physical separation $l_S$ of the associated reflection points, which is known in advance, to deduce the current relative permittivity of the medium, which can be converted directly into a moisture value when the associated material characteristic values are known.

The following holds:

$$\frac{\Delta D_S}{l_S} = \sqrt{\frac{\varepsilon'_R}{2}} \cdot \sqrt{\sqrt{1+\left(\frac{\varepsilon''_R}{\varepsilon'_R}\right)^2}+1}$$

where $\Delta D_S$ is the separation of the two echoes of the tensioning weight in the echo curve $l_S$ is the physical length of the tensioning weight Taking into account already known material-specific or negligibly small characteristic values for the imaginary part of the relative permittivity, the real part of the relative permittivity can be determined by transformation and can be used to directly deduce the moisture content of the medium according to the relationships already disclosed.

It may also be a special feature of the measuring instrument 501 that the echo-curve can be acquired in the radio frequency unit 502 in a particularly energy-saving manner by means of a sequential sampling technique. This results in a significant power saving compared with direct time-measurement techniques such as those that can be used in pure moisture meters, allowing the combined sensor to be designed as a two-wire measuring instrument. Further advantages of the sequential sampling technique also include an increased dynamic response, which also allows detection of very small echoes, and a higher measurement rate.

Since the stored material distances lie in the range of a few centimetres to several metres, and the propagation speed of electromagnetic waves even in a medium is close to the speed of light, the radio frequency signal transit times lie in the range of a few nanoseconds. In order to be able to measure these signals very accurately, a suitable approach is to expand by several orders of magnitude the voltage curve of the received electrical signal which represents the reflection conditions along the propagation direction of the electromagnetic wave.

This is done by means of a sequential sampling technique in which the transmitted/received signal is sampled periodically at temporally equidistant intervals. If the sample time is continually offset with respect to the transmission time, when combined the individual samples recreate an image of the original signal, albeit now a time-expanded image. The defined offset of the sample time with respect to the transmission time is vital to obtaining a uniformly constant, error-free time expansion. The result of this technique is an echo curve (406, 507), which is advantageously sampled over a time period of a few milliseconds and stored in the memory of a processor.

The embodiments of the measuring instrument presented so far allow an average moisture value to be determined, as can also be determined using other measuring instruments.

FIG. 6 shows another embodiment of a measuring apparatus according to an embodiment of the invention. The measuring instrument 600, unlike the measuring instrument 501, can have a waveguide apparatus consisting of at least two lines 601, 602. It may also be possible to use other probes as the waveguide apparatus, for example a rod probe, a coaxial probe or a probe consisting of a cable.

The two lines may be positioned at a defined distance from one another by regularly arranged spacers 603. The spacers can be formed by any insulating materials. For example, plastics materials that have a high mechanical strength can be used.

The measuring instrument acquires an echo curve 611 as in the above-mentioned examples in a known manner. The individual spacers each separately reflect some of the microwave energy, which is represented by echoes 607 in a correspondingly regular arrangement in the echo curve.

The separation $k_1$, $k_2$, etc. of the respective echoes in the echo curve corresponds, up to the actual stored-material echo 617, to the physically present separation of the spacers 603, which is known in advance. Below the stored material level, i.e. at distances greater than the distance to the stored-material surface, the microwaves experience a reduction in the propagation speed, which depends, inter alia, on the moisture content of the medium in the segment through which the microwaves are passing. The physically constant separation k between the spacers 603, 604, 605, 606 covered by the stored material 108 is depicted in the echo curve by different measured distances $K_u$, $K_v$, $K_w$ 608, 609, 610.

The moisture calculation unit 616 can determine from each of these distances, depicted having an increased length, a respective moisture value F(d) (612, 613, 614) of the material at the corresponding distance d from the measuring instrument. The procedure for evaluating the individual separations $K_i$ corresponds to the procedure described above for analysing the two echoes from a tensioning weight. The formulas described there apply analogously also to the case of two adjacently arranged discontinuities on the probe. The moisture value F calculated in each case can be assigned to the distance at the centre between the spacers concerned.

Interpolation techniques can be used to determine from the calculated characteristic values 612, 613, 614 a complete moisture profile 615 of the medium in the container, and can be provided at the interface 506 of the sensor in analogue and/or digital form.

This principle can also be applied to single conductors, coaxial conductors or hollow conductors by providing discontinuities at intervals along the coaxial conductor or hollow conductor.

The determination of the moisture content of a medium using electromagnetic waves can be further improved by taking into account the temperature of the medium.

FIG. 7 shows corresponding embodiments. The measuring instrument 701 comprises for this purpose a temperature sensor 706 that is installed in the sensor and is connected to the moisture calculation unit 704. The temperature values measured in the sensor provide a first approximation of the actual temperature of the medium 104 in the container, and can significantly improve the determination of the moisture value on the basis of the echo curve 406 acquired by the sensor.

The change in the relative permittivity for different media depending on the temperature is known in advance and can be obtained from the corresponding standard references for microwave measurement technology. The dependencies can be hardcoded into the instrument during manufacture, so that the temperature compensation curves can be directly accessed during operation.

The measuring instrument 701 can be designed as a radar level indicator, which can determine a three-dimensional or at least two-dimensional moisture profile. To do this, the radar level indicator scans the surface of the stored material (bulk solid) and thereby acquires a series of echo curves, each echo curve corresponding to a different main emission direction of the radar level indicator antenna. From each echo curve, it is possible to determine the moisture content of the stored product in a specific region of the stored product (through which the respective main emission direction runs). Thus a moisture distribution, i.e. a 2D or 3D moisture profile of the stored product, is obtained from the different moisture contents determined in this manner.

Further improvements result when using a non-contact temperature measuring unit 707, as used in a further apparatus 702. The temperature measuring unit 707, produced for example as an infrared thermometer, determines the temperature at the surface 709 of the medium to be measured in a non-contact manner, and forwards this temperature to the moisture calculation unit 704, which can now calculate the moisture content of the medium 104 with even greater accuracy.

When using guided microwaves, there are further options for direct, contacting measurement of the temperature of the medium 104. The apparatus 703 uses for this purpose one or more temperature sensors 708 installed over the length of the waveguide apparatus 710 (which may be the measuring apparatus 202 of FIG. 5 or the measuring apparatus 601-606 of FIG. 6), which sensors are interconnected via a bus system, for example, via which the moisture calculation unit 705 can directly read the temperature or a plurality of temperatures within the medium 104 and can use said temperatures to very accurately calculate the moisture content of the medium. FIG. 7 shows a development of the measuring apparatus of FIG. 5. Of course this can also be used, however, as already mentioned, to further improve a measuring apparatus according to FIG. 6.

The individual temperature sensors can be installed directly in the waveguide apparatus 710, for example directly during manufacture of the corresponding cable 710 or when attaching corresponding tensioning weights 204. In particular, the temperature measuring device can be attached directly in or on the tensioning weight 204. It may also be possible to position a temperature measuring device, which is arranged in parallel with the waveguide apparatus 202, 710, that allows at least one temperature of the medium 104 to be measured.

FIG. 8 shows a flow diagram of a method. In step 801, a measurement signal is generated. In step 802, the level is then determined from an echo curve of the measurement signal. In step 803, which can be performed before, after or at the same time as step 802, a moisture content of the stored product is determined from the echo curve. During the method, the measuring instrument is supplied with electrical power solely via a two-wire interface (for example 4 . . . 20 mA). In step 804, at least one of the measured values, selected from the group of measured level and moisture-content values, is output via the two-wire interface.

In addition, it should be mentioned that the terms "comprising" and "having" do not exclude any other elements or steps, and "a" or "an" does not rule out a plurality. It should also be pointed out that features or steps that have been described with reference to one of the above embodiments can also be used in combination with other features or steps of other embodiments described above. Reference signs in the claims shall not be deemed to have a limiting effect.

The invention claimed is:

1. A level measuring instrument for determining a level of a stored bulk material, comprising:
   a radio frequency unit generating a measurement signal;
   a signal processing unit determining the level of the stored bulk material from an echo curve of the measurement signal; and
   a temperature measuring device configured to acquire a temperature value to determine a temperature, the temperature measuring device being arranged in or on any one of i) a housing of the level measuring instrument or ii) a probe of the level measuring instrument;
   wherein the level measuring instrument determines, using the echo curve, a moisture content of the stored bulk material, the determining of the moisture content being based on an echo separation between echoes of the echo curve; and
   wherein the level measuring instrument improves, using the acquired temperature value, the accuracy with which the moisture content of the stored bulk material is deteimined.

2. The level measuring instrument according to claim 1, further comprising:
   a two-wire interface,
   wherein the level measuring instrument is supplied with power and outputs the measured level and moisture-content values, via the two-wire interface.

3. The level measuring instrument according to claim 2, further comprising:
   a data interface,
   wherein the level measuring instrument is supplied with power and outputs a first measured value, selected from the group of measured level and moisture-content values, via the two-wire interface; and
   wherein the level measuring instrument outputs a second measured value, selected from the group of measured level and moisture-content values, via the data interface.

4. The level measuring instrument according to claim 1, wherein the measurement signal is an FMCW signal.

5. The level measuring instrument according to claim 1, wherein the measurement signal is an electromagnetic pulse.

6. The level measuring instrument according to claim 1, wherein the level measuring instrument uses electromagnetic waves radiating into free space as the measurement signal.

7. The level measuring instrument according to claim 1, wherein the level measuring instrument uses guided microwaves as the measurement signal.

8. The level measuring instrument according to claim 7, comprising:
   a waveguide apparatus including a plurality of reflectors spaced apart from one another along a longitudinal extension direction of the waveguide apparatus,
   wherein the level measuring instrument determines a moisture profile from the echo curve and along the waveguide apparatus.

9. The level measuring instrument according claim 1, wherein the temperature measuring device is arranged as per any one of i) on and outside the housing of the level measuring device or ii) in or on the probe of the level measuring device.

10. The level measuring instrument according to claim 1, wherein the temperature measuring device is arranged in or on the probe of the level measuring device.

11. The level measuring instrument according to claim 10, wherein the probe includes a tensioning weight for tensioning at least one cable of the probe and wherein the temperature measuring device is arranged in or on the tensioning weight, the cable configured as a waveguide for guiding the measurement signal.

12. The level measuring instrument according to claim 10, wherein the determining the temperature is based on a length of the probe.

13. The level measuring instrument according to claim 1, wherein the temperature measuring device is configured and arranged to acquire the temperature of the stored bulk material.

14. The level measuring instrument according to claim 1, wherein the determining the temperature is based on the determined level of the material.

15. The level measuring instrument according to claim 1, wherein the determining the moisture content is based on a length of a tension weight of the probe.

16. The level measuring instrument according to claim 1, wherein the stored bulk material is granular.

17. A method for determining, using a level measuring device, a level of a stored bulk material, comprising the steps of:

generating a measurement signal;

determining the level of the stored bulk material from an echo curve of the measurement signal;

acquiring a temperature value to determine a temperature, the temperature value supplied by a temperature measuring device arranged in or on any one of i) a housing of the level measuring device or ii) a probe of the level measuring device; and using the temperature value, determining a moisture content of the stored bulk material from the echo curve, the determining of the moisture content being based on an echo separation between echoes of the echo curve.

18. The method according to claim 17, further comprising the step of:

supplying an electrical power, via a 4 . . . 20 mA two-wire interface, to an instrument performing the method.

19. The method according to claim 18, further comprising the step of:

outputting the measured level and moisture-content values, via the two-wire interface.

20. A program element, which, when executed on a processor, instructs the processor to perform determining steps of a method according to claim 17.

21. A non-transitory machine-readable medium on which a program element is stored which, when executed on a processor, instructs the processor to perform determining steps of a method according to claim 17.

* * * * *